(12) United States Patent
Kwon et al.

(10) Patent No.: US 10,524,749 B2
(45) Date of Patent: Jan. 7, 2020

(54) METHOD AND DEVICE FOR DIAGNOSIS OF BREAST DISEASE

(71) Applicant: INDUSTRIAL EDUCATION COOPERATION ORGANIZATION, DAEGU HEALTH COLLEGE, Daegu (KR)

(72) Inventors: Soon Mu Kwon, Daegu (KR); Yeong Han Kang, Daegu (KR); Kwon Su Chon, Gyeongsan-si (KR)

(73) Assignee: INDUSTRIAL EDUCATION COOPERATION ORGANIZATION, DAEGU HEALTH COLLEGE, Daegu (KR)

( * ) Notice: Subject to any disclaimer, the term of this patent is extended or adjusted under 35 U.S.C. 154(b) by 210 days.

(21) Appl. No.: 15/742,466

(22) PCT Filed: Jan. 15, 2016

(86) PCT No.: PCT/KR2016/000418
§ 371 (c)(1),
(2) Date: Jan. 5, 2018

(87) PCT Pub. No.: WO2017/082471
PCT Pub. Date: May 18, 2017

(65) Prior Publication Data
US 2018/0184993 A1   Jul. 5, 2018

(30) Foreign Application Priority Data

Nov. 12, 2015  (KR) .................. 10-2015-0159126

(51) Int. Cl.
*A61B 6/00*  (2006.01)
*A61B 5/00*  (2006.01)
(Continued)

(52) U.S. Cl.
CPC .......... *A61B 6/4417* (2013.01); *A61B 5/0091* (2013.01); *A61B 5/015* (2013.01);
(Continued)

(58) Field of Classification Search
CPC .......... A61B 6/00; A61B 6/06; A61B 6/4417; A61B 6/502; A61B 6/54; A61B 6/5247;
(Continued)

(56) References Cited

U.S. PATENT DOCUMENTS

2007/0161922 A1   7/2007  Dekel et al.
2012/0050321 A1   3/2012  Arieli et al.

FOREIGN PATENT DOCUMENTS

KR   10-0804809 B1   2/2008
KR   10-2012-0127068 A   11/2012
(Continued)

*Primary Examiner* — Jurie Yun
(74) *Attorney, Agent, or Firm* — Novick, Kim & Lee, PLLC; Jae Youn Kim (57) ABSTRACT

The present invention relates to a method and a device for diagnosis of breast disease and, more specifically, to an X-ray mammography device and method, which allow positions of an X-ray radiation field and a thermogram acquisition means to be controlled such that the center axis of the X-ray radiation field and a visual axis of the thermogram acquisition means are the same, so as to acquire each of a mammogram and a breast thermogram having the same center, and generates a fusion image so as to obtain a structural image and an image of a physiological change (body temperature and the activity of blood vessels) of breast tissue, thereby improving an early diagnosis and diagnosis ability for breast disease.

6 Claims, 9 Drawing Sheets

(51) Int. Cl.
 *A61B 5/01* (2006.01)
 *A61B 6/06* (2006.01)
(52) U.S. Cl.
 CPC .............. *A61B 6/502* (2013.01); *A61B 6/54* (2013.01); *A61B 6/06* (2013.01); *A61B 6/5247* (2013.01)
(58) Field of Classification Search
 CPC ......... A61B 6/542; A61B 6/544; A61B 6/405; A61B 5/00; A61B 5/01; A61B 5/0091; A61B 5/015; A61B 5/02; A61B 5/02007; A61B 5/021; A61B 5/026
 USPC ...... 378/37, 62, 63, 147, 149, 150, 151, 152
 See application file for complete search history.

(56) References Cited

FOREIGN PATENT DOCUMENTS

| | | |
|---|---|---|
| KR | 10-2015-0082970 A | 7/2015 |
| WO | 2004-102957 A1 | 11/2004 |

Mammogram  Breast thermogram  Fusion image

FIG. 13

METHOD AND DEVICE FOR DIAGNOSIS OF BREAST DISEASE

TECHNICAL FIELD

The present invention relates to a method and a device for diagnosing breast diseases, and more particularly, to a method and an apparatus for diagnosing breast diseases, which can control positions of an X-ray radiation field and a thermogram acquisition means such that the center axis of the X-ray radiation field and a visual axis of the thermogram acquisition means are the same so as to respectively acquire a mammogram and a thermogram of the breast at the same center, and generate a fusion image so as to obtain a structural image and an image of a physiological change of breast tissue, thereby improving an early diagnosis and diagnosis ability for breast diseases.

BACKGROUND ART

Breast cancer patients occupy 23% of female cancer patients all over the world. An early diagnosis is very important because breast cancer, which is the top female cancer killer in the case of females in their 30s to 40s, spreads well and the relapse rate is very high. Differently from the West, women in their 40s in Korea have the highest incidence rate of breast cancer, and a ratio of breast cancer patients of pre-menopausal females reaches 60% and is three times higher than that of the West. Therefore, Korea executes a regular diagnosis at a national level for prevention and early diagnosis of breast cancer.

As devices for diagnosing breast diseases, a mammography scanner and an ultrasound imaging device have been mainly used, and a magnetic resonance imaging (MRI) system and a thermography scanner have been also used.

The mammography scanner is a device to irradiate X-rays onto a patient's body which is an examination object, detect a difference in energy intensity distribution of X-rays, which penetrate through the human body and are obtained by an X-ray detector, and to output it into an image.

Such a mammogram, which is an anatomical and structural image of abnormal tissue, is a breast cancer screening conducted to women after their 40s to 45s in most countries for the purpose of early diagnosis of breast cancer. However, such breast mammography increases an occurrence risk of breast cancer because radiation dose of the breast mammography is 100 times higher than that of tomography. Moreover, in the case of pre-menopausal women, women with large or small breasts, women with breasts in which prosthesis is implanted, women who is in hormone replacement therapy, women with a breast fibrocystic disease, or women anamnesis of biopsy, there are many limitations in application. In the case of dense breasts mostly observed in Asian women, it is low in lesion detection rate, and it is difficult to observe micro-calcification mainly observed in malignant tumor.

Furthermore, studies show that thermography is a noninvasive and noncontact screening and breast thermogram has no radiation exposure and is higher in sensitivity and specificity on breast diseases in comparison with mammogram. Neovascularization in malignant tumor starts in tumor diameter of 0.15 mm and develops well in tumor diameter of 1 mm to 3 mm. Differently from normal cells, nitric oxide generated in a tumor cell expands the diameter of the blood vessel and increases a blood flow rate. Therefore, Thermography can scan changes in body temperature and the activity of blood vessels, which are physiologic changes generated before a structural change of the breast tissue, such that a patient can be diagnosed in an early stage.

Recently, technologies to diagnose diseases complexly using various diagnosis devices have been developed. Korean Patent No. 10-0804809 discloses a technology using near-infrared rays and X-rays.

The conventional technology has X-rays and near infrared rays operated separately so as to scan a pectoral muscle part and an armpit part that X-rays cannot scan. However, technologies for scanning the same part related with breast diseases using various diagnosis methods have been not yet developed.

DISCLOSURE

Technical Problem

Accordingly, the present invention has been made in an effort to solve the above-mentioned problems occurring in the prior arts, and it is an object of the present invention to provide a method and an apparatus for diagnosing breast diseases, in which a thermogram camera is located on the same axis as the center axis of an X-ray radiation field so as to respectively acquire a mammogram and a thermogram of the breast and to output a fusion image, thereby providing an early diagnosis and an improved diagnosis ability through imaging structural changes and physiologic changes (body temperature and activity of blood vessels) of the breast tissue. Moreover, the method and the apparatus for diagnosing breast diseases according to the present invention allow one device to selectively acquire a single image, a parallel image and a fusion image according to patients or characteristics of diseases.

It is another object of the present invention to provide a method and an apparatus for diagnosing breast diseases, which can move a location of the thermogram camera not to act as an obstacle while the thermogram camera and an X-ray tube acquire a breast thermogram and a mammogram, thereby acquiring a clear breast thermogram and a clear mammogram.

It is a further object of the present invention to provide a method and an apparatus for diagnosing breast diseases, which can operate the breast thermogram before mammogram scanning to adjust an aperture according to the shape and size of an examination object, thereby obtaining an accurate image through reduction of unnecessary scattering and reducing an exposure dose of a human body.

Technical Solution

To achieve the above objects, the present invention provides a method for diagnosing breast diseases including: an image acquiring process of acquiring a breast thermogram and a mammogram through a breast thermography scanner and a mammography scanner by controlling locations of a mammography scanner and a breast thermography scanner such that the center axis of an X-ray radiation field and a visual axis of a thermogram camera are located on the same axis; and a process of fusing the acquired mammogram and breast thermogram into one image having the same center.

In the above, the process of acquiring the breast thermogram is achieved before acquisition of the mammogram, and the radiation field of an aperture of the mammography scanner is adjusted on the basis of the acquired breast thermogram.

Moreover, in another aspect of the present invention, the present invention provides an apparatus for diagnosing breast diseases including: a mammography scanner having an X-ray tube, an aperture for adjusting a radiation field of X-rays, and an X-ray detector for acquiring an X-ray image; a thermography scanner having a thermogram camera; a conveying means for controlling the location of the thermography scanner; an image fusion system for fusing the mammogram acquired from the mammography scanner and the breast thermogram acquired from the thermography scanner into one image; and a controller for controlling operations of the mammography scanner, the thermography scanner, and the conveying means such that the center axis of the radiation field and a visual axis of the thermogram camera are the same so as to acquire the mammogram and the breast thermogram.

The aperture has a plurality of leaves, and the leaves are adjusted in their locations by an operating means, such that the radiation field is adjusted according to the size and form of the breast acquired through the breast thermogram.

Advantageous Effects

As described above, the method and the apparatus for diagnosing breast diseases according to the present invention can accurately fuse a plurality of images into a single image because the center axis of the X-ray radiation field and the visual axis of the thermogram camera are the same and images obtained from the X-ray radiation field and the thermogram camera have the same center, and make an image of structural changes and physiologic changes (body temperature and activity of blood vessels) of the breast tissue, thereby providing an early diagnosis and an improved diagnosis ability.

Furthermore, the method and the apparatus for diagnosing breast diseases according to the present invention can accurately adjust the radiation field of the aperture according to the shape and size of a breast image obtained through the thermogram camera, thereby obtaining an accurate image through reduction of unnecessary scattering and reducing an exposure dose of a human body.

Additionally, the method and the apparatus for diagnosing breast diseases according to the present invention can obtain accurate images because the thermogram camera which is movable in location does not act as an obstacle when acquiring a breast thermogram and a mammogram.

EXPLANATION OF ESSENTIAL REFERENCE NUMERALS IN DRAWINGS

110: X-ray tube
120: Thermography camera
122: Transferring means
130: Aperture
150: Image fusion system

MODE FOR INVENTION

Hereinafter, reference will be now made in detail to preferred embodiments of the present invention with reference to the attached drawings.

An apparatus for diagnosing breast diseases according to an embodiment of the present invention includes: a mammography scanner A having an X-ray tube 110 for irradiating X-rays, an aperture 130 for adjusting a radiation field of X-rays, and an X-ray detector 140 for acquiring an X-ray image; a thermography scanner B having a thermogram camera 120 for acquiring a breast thermogram; a conveying means 122 for controlling the location of the thermography scanner B; an image fusion system 150 for fusing the mammogram acquired from the X-ray detector 140 and the breast thermogram acquired from the thermogram camera 120 into one image; and a controller 160 for controlling operations of the mammography scanner A, the thermography scanner B, the conveying means 122, and the image fusion system 150 so as to acquire and fuse the mammogram and the breast thermogram such that the center axis of the radiation field and a visual axis of the thermogram camera are the same. Therefore, the apparatus for diagnosing breast diseases according to the embodiment of the present invention can provide accurate breast scanning and diagnosis.

Figure 1:
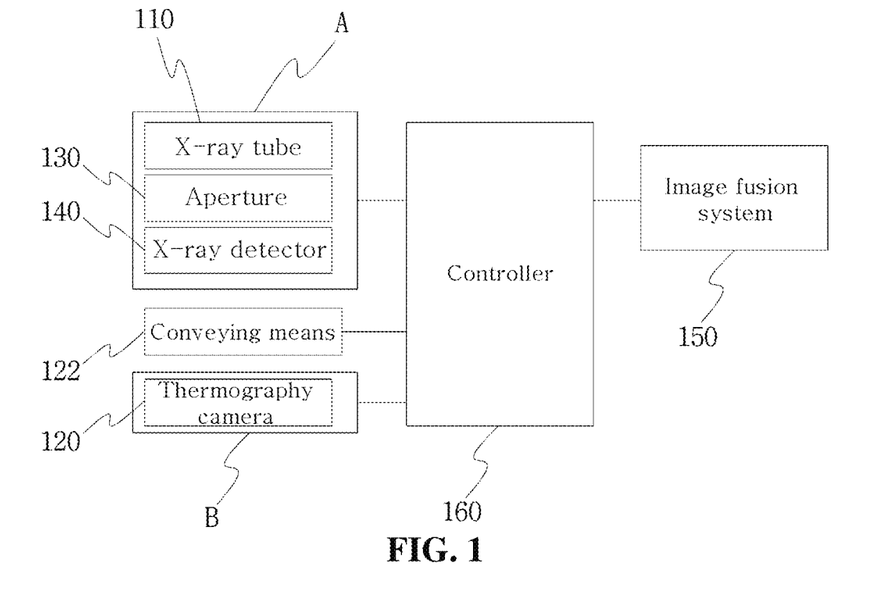
FIG. 1 is a view showing a conventional mammogram system.
Figure 2:
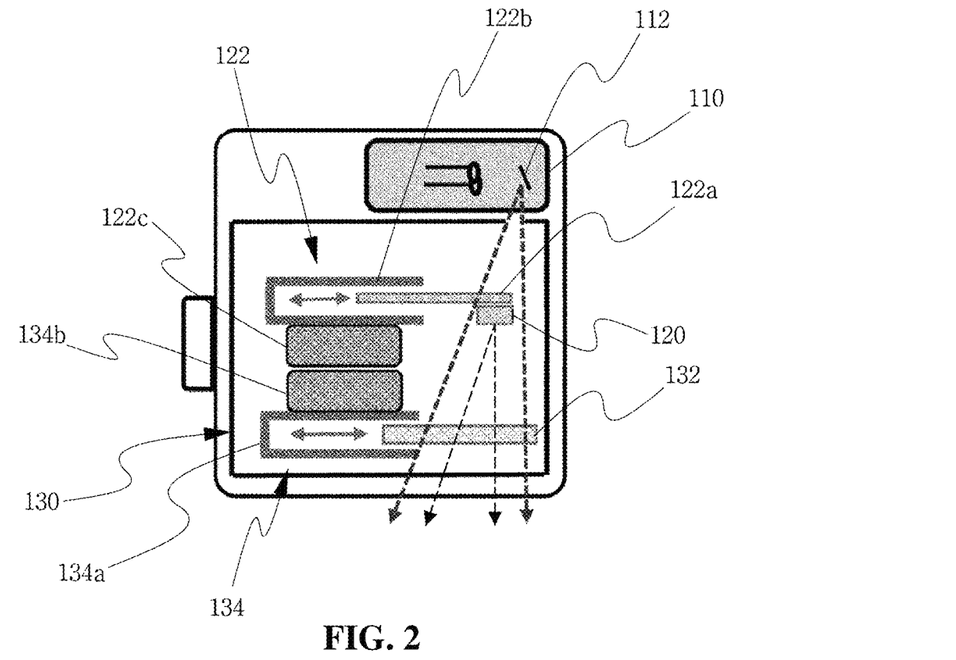
FIG. 2 is a view showing a conventional aperture.

That the center axis of the radiation field and a visual axis of the thermogram camera are the same means that the center of a radiation angle of a reflector 112, which reflects the X-rays irradiated from the X-ray tube 110 to an examination object, and the center of a radiation angle of the thermogram camera 120 coincide with each other, as indicated by dotted arrows in FIG. 2.

In more detail, the conveying means 122 moves the location of the thermogram camera 120 such that the center axis of the radiation field and the visual axis of the thermogram camera coincide with each other.

Figure 3:
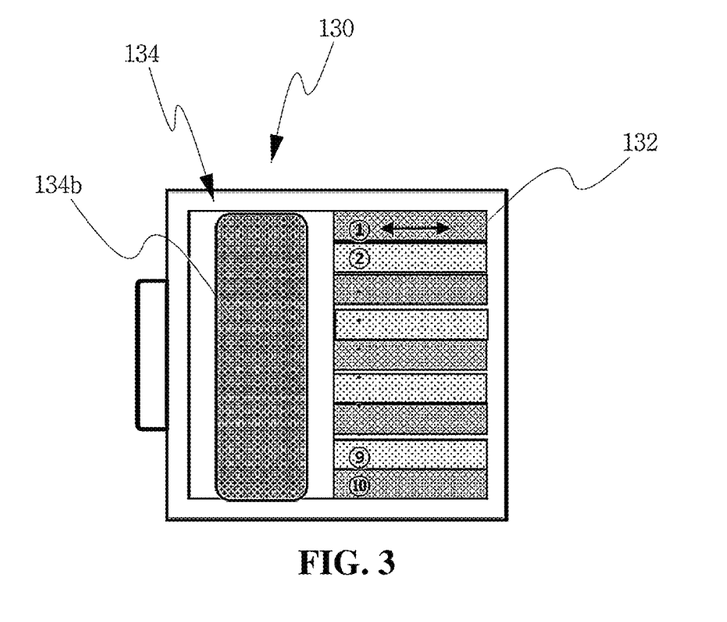
FIG. 3 is a view showing a radiation field by the conventional aperture.

As shown in FIGS. 2 and 3, the apparatus for diagnosing breast diseases according to an embodiment of the present invention includes: a mammography scanner A having an X-ray tube 110 for irradiating X-rays, and an aperture 130, which consists of a plurality of leaves 132 and is arranged below an X-ray tube 110 in such a way that the leaves 132 are independently movable by an operating means 134; a thermography scanner B having a thermogram camera 120, which is arranged between the X-ray tube 110 and an examination object and is moved by a conveying means 122 to acquire a breast thermogram, wherein the thermogram camera 120 is arranged below the X-ray tube 110 to acquire a breast thermogram of the examination object and is removed from below the X-ray tube at the time of mammography scanning after acquiring the breast thermogram; and a controller (not shown) for adjusting a movement amount of the leaves 132 of the aperture 130 according to the shape and size of the examination object acquired from the breast thermogram and outputting one fusion image by transferring the acquired mammogram and breast thermogram to an image fusion system 150.

The conveying means 122 includes: a conveying board 122a on which the thermogram camera 120 is mounted at a front end thereof; a guide 122b for guiding movement of the conveying board 122a; and a driving source 122c, such as a motor or a cylinder, for moving the conveying board 122a along the guide 122b.

As shown in FIGS. 2 and 3, the aperture 130 has a plurality of the leaves 132 arranged in one direction, and the operating means 134 controls the movement amount of the leaves 132. For this, a guide 134a for guiding the movement of each leave 132 is formed and a driving source 134b, such as a motor, is disposed on each leaf 132. Such a movement amount control structure may be changed in various ways by those skilled in the art, and so, a detailed description of the movement amount control structure will be omitted.

Moreover, the guide 134a for guiding the movement of the leaves 132 is located above and below the leaves 132 as shown in FIG. 2 not to obstruct movement of the leaves arranged horizontally because the leaves 132 are arranged on the same line horizontally.

Figure 4:
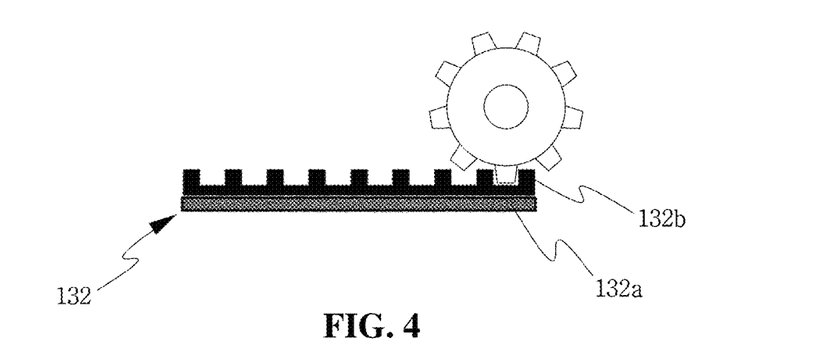
FIG. 4 is a view showing a mammography system according to an embodiment of the present invention.

In the meantime, the leaves 132 are mainly made of tungsten or lead in order to shield X-rays. In this instance, because tungsten is not easy to work and lead is high in abrasivity by operation, as shown in FIG. 4, the leaf is formed to have a double structure of a tungsten layer or a lead layer 132a and a stainless steel layer 132b. In this instance, for instance, in the case that the leaves are moved in the back-and-forth direction in a rack-and-pinion structure, rack working necessary for the stainless steel layer is carried out.

Figure 5:
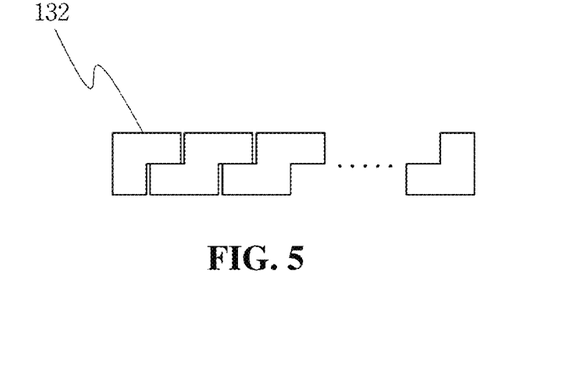
FIG. 5 is a view showing an aperture according to the embodiment of the present invention.
Figure 6:
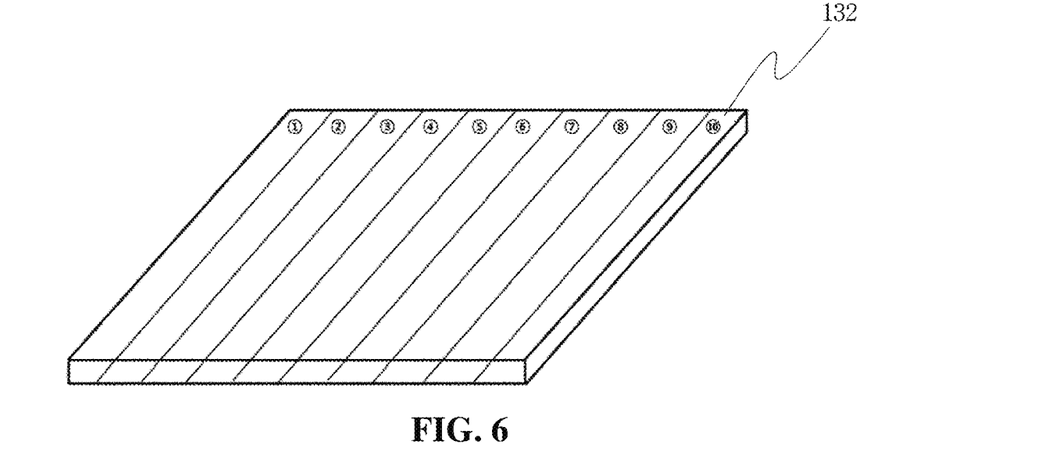
FIG. 6 is a view showing a cross-sectional structure of leaves according to the embodiment of the present invention.
Figure 7:
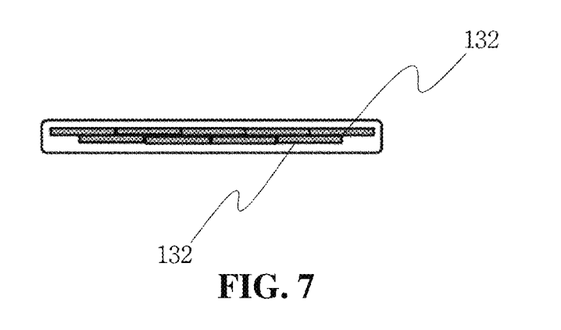
FIGS. 7 to 9 are views showing a side section structure of the leaves.

Furthermore, because a plurality of the leaves 132 are arranged, as shown in FIG. 5, both end portions of each leaf 132 are formed to be stepped such that neighboring side surfaces of the leaves 132 are overlapped each other so as to block penetration of X-rays through their boundaries. Alternatively, both sides of the leaves are formed to be inclined as shown in FIG. 6, or the leaves are arranged in a zigzag form in two rows of an upper part and a lower part such that boundary parts of the leaves are not even vertically as shown in FIG. 7.

Figure 8:
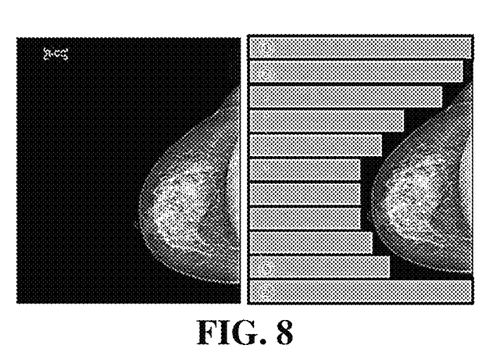
Figure 9:
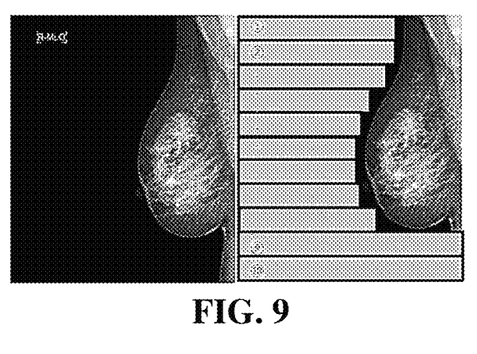

As shown in FIGS. 8 and 9, the aperture having the leaves 132 can obtain a radiation field suitable for the shape and size of the examination object.

Figure 10:
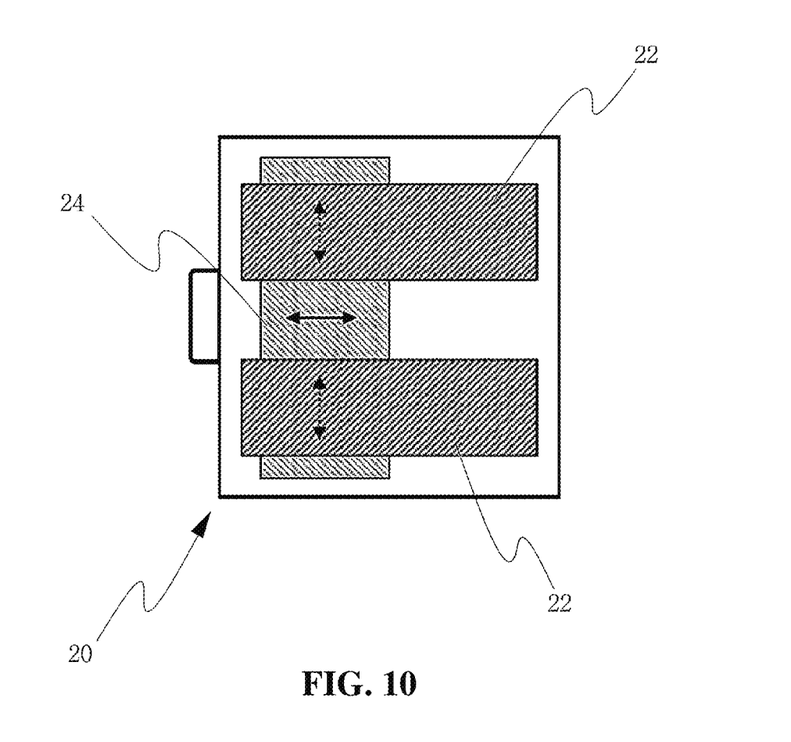
FIG. 10 is a views showing a mammography system according to another embodiment of the present invention.
Figure 11:
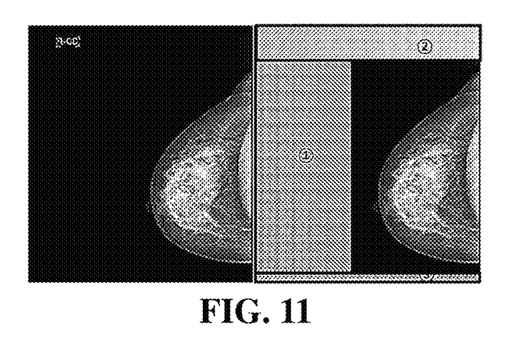
FIGS. 11 to 12 are views showing a radiation field according to the present invention.

In the meantime, the aperture may not have the structure that a plurality of leaves are arranged like the conventional structure as shown in FIG. 10, but may adopt a way that one plate-type leaf 22 adjust an area where X-rays are irradiated in the form of a rectangle as shown in FIG. 11 while moving in the X-axis direction (from side to side) and in the Y-axis direction (from top to bottom).

Figure 12:
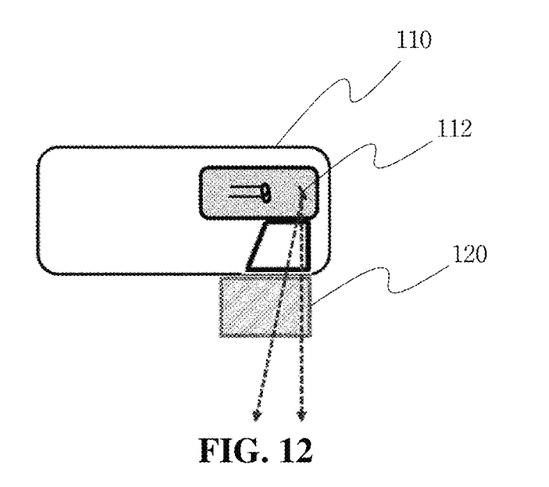
Figure 13:
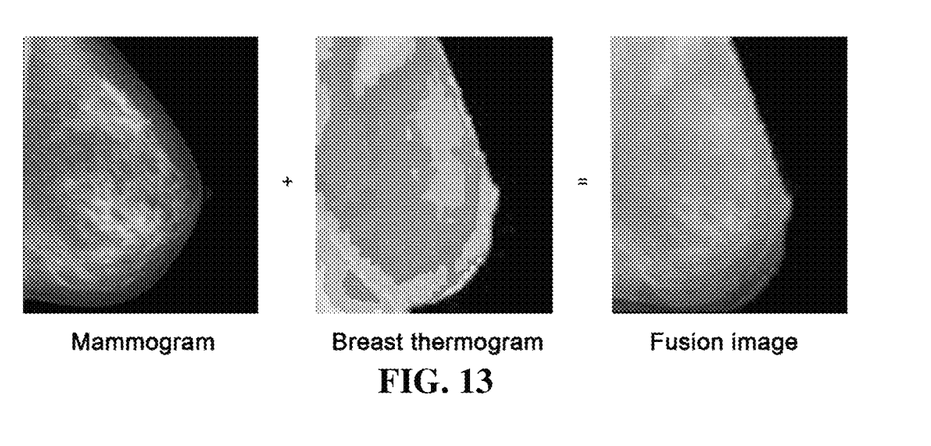
FIG. 13 is a view showing an example of output of breast thermogram according to the present invention.

Additionally, as shown in FIG. 2, the thermogram camera and the aperture may be formed integrally inside the X-ray tube and one case, or may be formed in a separate module so as to be attached to a lower part of the X-ray tube of a conventional X-ray examination device as shown in FIG. 12.

Meanwhile, a method for diagnosing breast diseases according to an embodiment of the present invention includes: an image acquiring process of acquiring a breast thermogram and a mammogram by controlling locations of a mammography scanner and a breast thermography scanner such that the center axis of an X-ray radiation field and a visual axis of a thermogram camera are located on the same axis; and a process of fusing and outputting the acquired mammogram and breast thermogram into one image having the same center.

The process of acquiring breast thermogram is achieved before acquisition of mammogram, and the radiation field of the aperture is adjusted on the basis of the acquired breast thermogram.

The method for diagnosing breast diseases will be described in more detail using the apparatus for diagnosing breast diseases.

First, the controller locates the thermogram camera 120 below the X-ray tube 110 before mammogram scanning, and arranges mammography scanner and a breast thermography scanner such that the center axis of the X-ray radiation field and the visual axis of the thermogram camera are located on the same axis so as to scan the examination object. The images are transferred to the image fusion system. In this instance, the controller acquires a contour line of the examination object to recognize the shape and size of the examination object. When the shape and size of the examination object is recognized, the controller adjusts the movement amount of the leaves of the aperture to adjust the X-ray radiation field according to the shape and size of the examination object, and then, removes the thermogram camera from below the X-ray tube.

The apparatus for diagnosing breast diseases executes mammogram scanning to acquire a mammogram after the radiation field is secured and obstacles are removed, and then, transfers the mammogram to the image fusion system.

Additionally, the image fusion system fuses the breast thermogram and the mammogram into one image through an image processor, and then, outputs to PACS.

In the above process, because the centers of the breast thermogram and the mammogram are the same, images of the examination object may be different in size according to scanning positions. However, because the centers of the images are the same, the image processor can correct and fuse a plurality of the images into the same size through magnification of the images according to the scanning positions so as to acquire a fusion image matched accurately, such that the apparatus for diagnosing breast diseases according to the present invention can make an accurate diagnosis through the obtained fusion image.

The invention claimed is:

1. An apparatus for diagnosing breast diseases, comprising:
    a mammography scanner having an X-ray tube for irradiating X-rays, an aperture for adjusting a radiation field of X-rays, and an X-ray detector for acquiring a mammogram;
    a thermography scanner having a thermogram camera for acquiring a breast thermogram;
    a conveying means for controlling a location of the thermography scanner;
    an image fusion system for fusing the mammogram acquired from the X-ray detector and the breast thermogram acquired from the thermogram camera into one image; and
    a controller for controlling operations of the mammography scanner, the thermography scanner, the conveying means, and the image fusion system such that the center axis of the radiation field and a visual axis of the thermogram camera are the same and such that acquisition of the breast thermogram is achieved before acquisition of the mammogram, and a radiation field of an aperture of the mammography scanner is adjusted on the basis of the acquired breast thermogram, and for transferring the acquired mammogram and breast thermogram to the image fusion system, wherein the aperture includes a plurality of leaves and is arranged below the X-ray tube in such a way that the leaves are independently movable by an operating means.

2. The apparatus for diagnosing breast diseases according to claim 1, the leaves are formed to have a double structure of a tungsten layer or a lead layer and a stainless steel layer, and the stainless steel layer is worked.

3. The apparatus for diagnosing breast diseases according to claim 1, both end portions of the leaves are formed to be stepped such that neighboring side surfaces of the leaves are overlapped with each other.

4. The apparatus for diagnosing breast diseases according to claim 1, both sides of each leaf are formed to be inclined.

5. The apparatus for diagnosing breast diseases according to claim 1, the leaves are arranged in a zigzag form in two rows of an upper part and a lower part such that boundary parts of the leaves are not even vertically.

6. A method for diagnosing breast diseases, comprising:

acquiring a breast thermogram and a mammogram by controlling locations of a mammography scanner and a breast thermography scanner by a controller such that the center axis of an X-ray radiation field of an X-ray tube and a visual axis of a thermogram camera are located on the same axis; and fusing and outputting the acquired mammogram and breast thermogram into one image having the same center by an image fusion system;

wherein acquisition of the breast thermogram is achieved before acquisition of the mammogram, and a radiation field of an aperture of the mammography scanner is adjusted on the basis of the acquired breast thermogram.

* * * * *